US011365397B2

(12) United States Patent
Wei et al.

(10) Patent No.: US 11,365,397 B2
(45) Date of Patent: Jun. 21, 2022

(54) METHODS FOR SCREENING PERSONAL CARE PRODUCTS (71) Applicant: The Procter & Gamble Company, Cincinnati, OH (US)

(72) Inventors: Karl Shiqing Wei, Mason, OH (US); Teresa DiColandrea, Wyoming, OH (US); Deborah Ruth Finlay, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 285 days.

(21) Appl. No.: 16/697,946

(22) Filed: Nov. 27, 2019

(65) Prior Publication Data

US 2020/0172876 A1   Jun. 4, 2020

Related U.S. Application Data (60) Provisional application No. 62/772,711, filed on Nov. 29, 2018.

(51) Int. Cl.
*C12N 5/071* (2010.01)
*G01N 33/50* (2006.01)

(52) U.S. Cl.
CPC ......... *C12N 5/0698* (2013.01); *C12N 5/0629* (2013.01); *G01N 33/5008* (2013.01); *G01N 33/5064* (2013.01); *G01N 33/5082* (2013.01); *C12N 2502/094* (2013.01); *C12N 2513/00* (2013.01); *G01N 2500/10* (2013.01)

(58) Field of Classification Search
None
See application file for complete search history.

(56) References Cited

U.S. PATENT DOCUMENTS

| | | |
|---|---|---|
| RE3,300 E | 2/1869 | McGill |
| RE3,315 E | 3/1869 | Merrill |
| 2,020,454 A | 11/1935 | Spaulding |
| 2,438,091 A | 3/1948 | Lynch |
| 2,528,378 A | 10/1950 | Mccabe, Jr. |
| 2,658,072 A | 11/1953 | Kosmin |
| 2,798,053 A | 7/1957 | Brown |
| 2,986,271 A | 5/1961 | Forrer |
| 3,455,440 A | 7/1969 | West |
| 3,479,429 A | 11/1969 | Morshauser |
| 3,533,955 A | 10/1970 | Pader |
| 3,542,256 A | 11/1970 | Waterman |
| D220,248 S | 3/1971 | Blumenthal |
| 3,618,757 A | 11/1971 | Funkhouser |
| 3,800,898 A | 4/1974 | Griffin |
| 3,850,365 A | 11/1974 | Dietrich |
| 3,852,475 A | 12/1974 | Tarangul |
| 3,899,076 A | 8/1975 | Florian |
| 3,915,921 A | 10/1975 | Schlatzer, Jr. |
| 3,926,861 A | 12/1975 | Gerecht |
| 3,929,678 A | 12/1975 | Laughlin et al. |
| 3,937,811 A | 2/1976 | Papantoniou |
| 3,940,351 A | 2/1976 | Schlatzer, Jr. |
| 3,951,679 A | 4/1976 | Bernhard |
| 3,980,767 A | 9/1976 | Chown |
| 4,062,817 A | 12/1977 | Westerman |
| 4,159,028 A | 6/1979 | Barker |
| 4,263,363 A | 4/1981 | Buck |
| 4,335,103 A | 6/1982 | Barker |
| 4,379,753 A | 4/1983 | Bolich, Jr. |
| 4,384,096 A | 5/1983 | Sonnabend |
| 4,421,902 A | 12/1983 | Chang |
| 4,425,322 A | 1/1984 | Harvey |
| 4,429,097 A | 1/1984 | Chang |
| 4,514,552 A | 4/1985 | Shay |
| 4,518,578 A | 5/1985 | Hayes |
| 4,600,761 A | 7/1986 | Ruffner |
| 4,616,074 A | 10/1986 | Ruffner |
| D292,879 S | 11/1987 | Smith |
| 4,743,698 A | 5/1988 | Ruffner |
| 4,772,427 A | 9/1988 | Dawson |
| 4,814,160 A | 3/1989 | Carter |
| 4,879,114 A | 11/1989 | Catsimpoolas |
| 4,966,205 A | 10/1990 | Tanaka |
| 4,980,155 A | 12/1990 | Shah |
| 5,002,680 A | 3/1991 | Schmidt |
| 5,011,681 A | 4/1991 | Ciotti |
| 5,059,414 A | 10/1991 | Dallal |
| 5,104,646 A | 4/1992 | Bolich, Jr. |
| 5,106,609 A | 4/1992 | Bolich, Jr. |
| 5,135,748 A | 8/1992 | Ziegler |
| 5,147,576 A | 9/1992 | Montague |
| 5,223,315 A | 6/1993 | Katsura |

(Continued)

FOREIGN PATENT DOCUMENTS

| | | |
|---|---|---|
| CN | 1153468 A | 7/1997 |
| CN | 110804666 A | 2/2020 |

(Continued)

OTHER PUBLICATIONS

Fowler, Practical Dermatology, Jul. 2012, pp. 36-40. (Year: 2012).*
Fluhr et al, Skin Research and Technology, 1999, vol. 5, pp. 171-178. (Year: 1999).*
Maeno etal, Analytical Methods, Jul. 2017, vol. 9, pp. 4851-4857. (Year: 2017).*
Becker et al., Detection of Differentially Regulated Genes in Keratinocytes by cDNA Array Hybridization: Hsp27 and Other Novel Players in Response to Artificial Ultraviolet Radiation, Journal of Investigative Dermatology, vol. 116, No. 6, Jun. 2001, pp. 983-988.
Chng et al. Whole metagenome profiling reveals skin microbiome-dependent susceptibility to atopic dermatitis flare. NatureMicrobiology 2016, vol. 1, No. 16106, (Year: 2016), pp. 1-10.
Cocamidopropyl betaine Product Specification, Edition 1, Jun. 2005, p. 1-51.
Conti et al., Seasonal influences on stratum corneum ceramide 1 fatty acids and the influence of topical essential fatty acids, International Journal of Cosmetic Science 18, 1-12 (1996), 12 pgs.

(Continued)

*Primary Examiner* — Allison M Fox
(74) *Attorney, Agent, or Firm* — John G. Powell (57) ABSTRACT

Methods of screening rinse-off personal care compositions can include the use of explant skin in combination with measurements for moisture and/or cell proliferation.

11 Claims, 6 Drawing Sheets

(56) References Cited

U.S. PATENT DOCUMENTS

| | | |
|---|---|---|
| 5,228,912 A | 7/1993 | Herget |
| 5,292,843 A | 3/1994 | Jenkins |
| 5,294,692 A | 3/1994 | Barron |
| 5,304,334 A | 4/1994 | Lahanas |
| 5,308,526 A | 5/1994 | Dias et al. |
| 5,342,883 A | 8/1994 | Jenkins |
| 5,364,617 A | 11/1994 | Bush |
| 5,393,450 A | 2/1995 | Shana |
| 5,412,142 A | 5/1995 | Wilkerson, III |
| 5,455,035 A | 10/1995 | Guerrero |
| 5,462,963 A | 10/1995 | Bush |
| 5,487,168 A | 1/1996 | Geiner |
| 5,487,884 A | 1/1996 | Bissett |
| 5,523,619 A | 6/1996 | Mcallister |
| 5,540,853 A | 7/1996 | Trinh |
| 5,556,628 A | 9/1996 | Derian |
| 5,578,299 A | 11/1996 | Starch |
| 5,612,307 A | 3/1997 | Chambers |
| 5,632,420 A | 5/1997 | Lohrman |
| 5,635,171 A | 6/1997 | Nadaud |
| 5,652,228 A | 7/1997 | Bissett |
| 5,661,189 A | 8/1997 | Grieveson |
| 5,681,852 A | 10/1997 | Bissett |
| 5,687,779 A | 11/1997 | Andersson |
| 5,716,920 A | 2/1998 | Glenn, Jr |
| 5,770,760 A | 6/1998 | Robinson |
| 5,816,451 A | 10/1998 | Renault |
| 5,817,609 A | 10/1998 | He et al. |
| 5,851,978 A | 12/1998 | Shana |
| 5,873,494 A | 2/1999 | Dallas, Jr. |
| 5,874,495 A | 2/1999 | Robinson |
| 5,914,117 A | 6/1999 | Lavaud |
| 5,916,575 A | 6/1999 | Mcatee |
| 5,925,603 A | 7/1999 | D'Angelo |
| 5,929,019 A | 7/1999 | Puvvada |
| 5,947,335 A | 9/1999 | Milio |
| 5,952,286 A | 9/1999 | Puvvada |
| 5,954,213 A | 9/1999 | Gerhart |
| 5,965,500 A | 10/1999 | Puvvada |
| 5,965,501 A | 10/1999 | Rattinger |
| 5,965,502 A | 10/1999 | Balzer |
| 5,972,361 A | 10/1999 | Fowler |
| 6,051,386 A | 4/2000 | Lerner |
| 6,068,834 A | 5/2000 | Kvalnes |
| D426,158 S | 6/2000 | Underwood |
| 6,080,708 A | 6/2000 | Glenn, Jr. et al. |
| 6,110,883 A | 8/2000 | Petri et al. |
| 6,150,312 A | 11/2000 | Puvvada |
| 6,150,313 A | 11/2000 | Harmalker et al. |
| 6,165,395 A | 12/2000 | Kieras |
| 6,174,845 B1 | 1/2001 | Rattinger |
| 6,176,391 B1 | 1/2001 | Rehkemper |
| 6,190,648 B1 | 2/2001 | Kouzu |
| 6,194,364 B1 | 2/2001 | Glenn, Jr. |
| D438,460 S | 3/2001 | Hammond |
| D439,165 S | 3/2001 | Erckelbout |
| 6,213,166 B1 | 4/2001 | Thibiant |
| 6,217,888 B1 | 4/2001 | Oblong |
| D441,645 S | 5/2001 | Longhurst |
| 6,232,496 B1 | 5/2001 | Carr |
| 6,245,323 B1 | 6/2001 | Christie |
| 6,245,344 B1 | 6/2001 | Thibiant |
| 6,268,322 B1 | 7/2001 | St. Lewis |
| D446,121 S | 8/2001 | Maddy |
| 6,270,446 B1 | 8/2001 | Abelbeck |
| D448,678 S | 10/2001 | Bakic |
| 6,306,806 B1 | 10/2001 | St. Lewis |
| 6,335,312 B1 | 1/2002 | Coffindaffer |
| 6,338,855 B1 | 1/2002 | Albacarys |
| 6,340,723 B1 | 1/2002 | Nitta |
| D455,655 S | 4/2002 | Bunce |
| 6,367,519 B2 | 4/2002 | Thibiant |
| 6,383,999 B1 | 5/2002 | Coyle |
| 6,385,992 B1 | 5/2002 | Flore, Jr. |
| 6,394,323 B2 | 5/2002 | Mcclean |
| 6,395,691 B1 | 5/2002 | Tsaur |
| 6,407,044 B2 | 6/2002 | Dixon |
| 6,413,192 B2 | 7/2002 | Abelbeck |
| 6,419,783 B1 | 7/2002 | Rainey |
| 6,426,326 B1 | 7/2002 | Mitra |
| 6,429,177 B1 | 8/2002 | Williams |
| 6,433,061 B1 | 8/2002 | Marchant |
| D467,807 S | 12/2002 | Bakic |
| 6,495,498 B2 | 12/2002 | Niemiec |
| 6,506,391 B1 | 1/2003 | Biatry |
| 6,516,838 B2 | 2/2003 | Thibiant |
| 6,517,939 B1 | 2/2003 | Moini |
| 6,521,216 B1 | 2/2003 | Glandorf |
| 6,523,457 B1 | 2/2003 | Ancona |
| 6,534,456 B2 | 3/2003 | Hayward |
| 6,534,457 B2 | 3/2003 | Mitra |
| 6,534,458 B1 | 3/2003 | Kakizawa |
| 6,537,527 B1 | 3/2003 | Kvalnes |
| 6,547,063 B1 | 4/2003 | Zaveri |
| 6,555,509 B2 | 4/2003 | Abbas et al. |
| 6,564,978 B1 | 5/2003 | Safian |
| 6,574,985 B2 | 6/2003 | Fiore, Jr. |
| 6,589,509 B2 | 7/2003 | Keller |
| 6,635,702 B1 | 10/2003 | Schmucker-castner |
| 6,645,511 B2 | 11/2003 | Aronson |
| 6,652,134 B2 | 11/2003 | Lloyd |
| 6,660,251 B1 | 12/2003 | Buenger et al. |
| 6,663,855 B2 | 12/2003 | Frechet |
| 6,673,371 B2 | 1/2004 | Brown |
| 6,673,755 B2 | 1/2004 | Wei |
| 6,673,756 B2 | 1/2004 | Sonnenberg et al. |
| D486,398 S | 2/2004 | Lovell |
| 6,691,394 B1 | 2/2004 | Mcclean |
| 6,695,510 B1 | 2/2004 | Look |
| 6,716,440 B2 | 4/2004 | Aronson |
| 6,723,688 B1 | 4/2004 | Malik |
| 6,727,209 B2 | 4/2004 | Pereira |
| 6,752,982 B2 | 6/2004 | Colwell et al. |
| 6,759,376 B2 | 7/2004 | Zhang |
| 6,780,826 B2 | 8/2004 | Zhang |
| 6,849,584 B2 | 2/2005 | Geary |
| D502,400 S | 3/2005 | Cinquino |
| D505,079 S | 5/2005 | Mulder |
| 6,897,253 B2 | 5/2005 | Schmucker-castner |
| 6,916,791 B2 | 7/2005 | Holick et al. |
| 6,919,303 B2 | 7/2005 | Pham |
| 6,924,256 B2 | 8/2005 | Massaro |
| D525,872 S | 8/2006 | Haubert |
| D525,873 S | 8/2006 | Haubert |
| 7,084,104 B2 | 8/2006 | Martin |
| 7,098,180 B2 | 8/2006 | Ganopolsky |
| D527,637 S | 9/2006 | Bakic |
| D528,005 S | 9/2006 | Bakic |
| D529,388 S | 10/2006 | Bakic |
| D529,810 S | 10/2006 | Davies |
| 7,119,059 B2 | 10/2006 | Librizzi |
| D533,784 S | 12/2006 | Bakic |
| 7,143,893 B2 | 12/2006 | Kelly |
| 7,144,542 B2 | 12/2006 | Holzer |
| 7,157,414 B2 | 1/2007 | Librizzi |
| 7,229,486 B2 | 6/2007 | Wiersema |
| 7,229,778 B2 | 6/2007 | Hendrix |
| 7,268,104 B2 | 9/2007 | Krzysik |
| 7,273,837 B2 | 9/2007 | Boutique |
| 7,288,616 B2 | 10/2007 | Tamareselvy |
| 7,354,926 B2 | 4/2008 | Lintner |
| 7,488,707 B2 | 2/2009 | Frantz |
| 7,511,003 B2 | 3/2009 | Focht |
| 7,524,807 B2 | 4/2009 | Clapp |
| 7,527,077 B2 | 5/2009 | Mccall |
| 7,531,497 B2 | 5/2009 | Midha |
| 7,537,819 B2 | 5/2009 | Hendricks |
| D601,425 S | 10/2009 | Miller |
| D601,648 S | 10/2009 | Cornelio, Jr. |
| D608,648 S | 1/2010 | Rhodes |
| 7,649,047 B2 | 1/2010 | Tamareselvy |
| 7,666,824 B2 | 2/2010 | Krzysik et al. |
| 7,666,825 B2 | 2/2010 | Wagner |
| 7,737,104 B2 | 6/2010 | Hilliard, Jr. |

(56) References Cited

U.S. PATENT DOCUMENTS

| | | |
|---|---|---|
| 7,749,951 B2 | 7/2010 | Hilliard, Jr. |
| 7,754,666 B2 | 7/2010 | Walters |
| 7,754,667 B2 | 7/2010 | Walters |
| 7,761,242 B2 | 7/2010 | Honkonen |
| 7,763,419 B2 | 7/2010 | Hendrix |
| 7,767,389 B2 | 8/2010 | Hendrix |
| 7,771,924 B2 | 8/2010 | Hendrix |
| 7,771,925 B2 | 8/2010 | Hendrix |
| 7,776,346 B2 | 8/2010 | Oconnor |
| 7,803,403 B2 | 9/2010 | Librizzi |
| 7,820,609 B2 | 10/2010 | Soffin |
| 7,906,475 B2 | 3/2011 | Walters |
| 7,954,392 B2 | 6/2011 | Belcher |
| D641,633 S | 7/2011 | Carnduff |
| D644,106 S | 8/2011 | Almstead, Jr. |
| 8,025,902 B2 | 9/2011 | Librizzi |
| D646,170 S | 10/2011 | Carnduff |
| 8,029,772 B2 | 10/2011 | Frantz |
| 8,067,517 B2 | 11/2011 | Yoshinaka |
| 8,093,192 B2 | 1/2012 | Liu |
| 8,105,996 B2 | 1/2012 | Wei |
| 8,124,064 B2 | 2/2012 | Wei |
| 8,124,573 B2 | 2/2012 | Focht |
| 8,147,853 B2 | 4/2012 | Taylor |
| 8,158,566 B2 | 4/2012 | Wei |
| D660,181 S | 5/2012 | Nowacek |
| D660,704 S | 5/2012 | Simmons |
| D660,705 S | 5/2012 | Simmons |
| 8,283,852 B2 | 10/2012 | Lee |
| 8,309,667 B2 | 11/2012 | Yoshinaka |
| D674,282 S | 1/2013 | Baldridge |
| D674,292 S | 1/2013 | Klich |
| 8,394,361 B1 | 3/2013 | Frantz |
| 8,417,474 B2 | 4/2013 | Datta |
| D683,226 S | 5/2013 | Baldridge |
| 8,518,991 B2 | 8/2013 | Gunn |
| 8,772,212 B2 | 7/2014 | Restrepo et al. |
| 8,785,397 B2 | 7/2014 | Bernard |
| 8,795,679 B2 | 8/2014 | Einarsson |
| 8,840,871 B2 | 9/2014 | Wei |
| 9,101,551 B2 | 8/2015 | Stella |
| 9,162,085 B2 | 10/2015 | Dihora et al. |
| 9,176,144 B2 | 11/2015 | Donovan et al. |
| 9,186,642 B2 | 11/2015 | Dihora et al. |
| 9,216,143 B2 | 12/2015 | Restrepo et al. |
| 9,352,289 B2 | 5/2016 | Beijne et al. |
| 9,671,410 B2 | 6/2017 | Stella |
| 9,675,530 B2 | 6/2017 | Focht |
| 9,717,674 B1 | 8/2017 | Guskey |
| 9,750,674 B2 | 9/2017 | Wei |
| 9,808,408 B2 | 11/2017 | Stella |
| 9,931,282 B2 | 4/2018 | Restrepo et al. |
| 9,943,468 B2 | 4/2018 | Stevenson |
| 10,085,924 B2 | 10/2018 | Wei |
| 10,588,858 B2 | 3/2020 | Tamarkin |
| 10,942,107 B2 | 3/2021 | Wei et al. |
| 10,966,916 B2 | 4/2021 | Wei |
| 10,987,290 B2 | 4/2021 | Wei et al. |
| 2001/0006088 A1 | 7/2001 | Lyle |
| 2002/0042448 A1 | 4/2002 | Sorrentino |
| 2002/0122772 A1 | 9/2002 | Lukenbach |
| 2002/0182112 A1 | 12/2002 | Thorn |
| 2003/0003069 A1 | 1/2003 | Carson |
| 2003/0083210 A1 | 5/2003 | Goldberg |
| 2003/0147842 A1 | 8/2003 | Restle et al. |
| 2003/0161852 A1 | 8/2003 | Miller |
| 2003/0171230 A1 | 9/2003 | Shana'a et al. |
| 2003/0180246 A1 | 9/2003 | Frantz |
| 2003/0207988 A1 | 11/2003 | Tamareselvy |
| 2003/0232101 A1 | 12/2003 | Travis |
| 2004/0009138 A1 | 1/2004 | Kling |
| 2004/0028932 A1 | 2/2004 | Holzer |
| 2004/0057920 A1 | 3/2004 | Focht |
| 2004/0091445 A1 | 5/2004 | Dykstra |
| 2004/0092415 A1 | 5/2004 | Focht |
| 2004/0092425 A1 | 5/2004 | Boutique |
| 2004/0105827 A1 | 6/2004 | Grimm |
| 2004/0146475 A1 | 7/2004 | Peffly |
| 2004/0158940 A1 | 8/2004 | Wells |
| 2004/0180020 A1 | 9/2004 | Manelski |
| 2004/0219119 A1 | 11/2004 | Wei |
| 2004/0223929 A1 | 11/2004 | Clapp |
| 2004/0223939 A1 | 11/2004 | Clausen |
| 2004/0223991 A1 | 11/2004 | Wei |
| 2004/0223992 A1 | 11/2004 | Clapp |
| 2004/0232023 A1 | 11/2004 | Bansal |
| 2004/0235693 A1 | 11/2004 | Wei |
| 2004/0235702 A1 | 11/2004 | Hawkins |
| 2004/0248748 A1 | 12/2004 | Wei |
| 2004/0248749 A1 | 12/2004 | Mitra |
| 2005/0003975 A1 | 1/2005 | Browne |
| 2005/0019299 A1 | 1/2005 | Librizzi |
| 2005/0020468 A1 | 1/2005 | Frantz |
| 2005/0049172 A1 | 3/2005 | Lukenbach |
| 2005/0063930 A1 | 3/2005 | Carlsson |
| 2005/0070452 A1 | 3/2005 | Librizzi |
| 2005/0075256 A1 | 4/2005 | Librizzi |
| 2005/0100570 A1 | 5/2005 | Wei |
| 2005/0129759 A1 | 6/2005 | Sojka |
| 2005/0139574 A1 | 6/2005 | Simone |
| 2005/0143269 A1 | 6/2005 | Wei |
| 2005/0191709 A1 | 9/2005 | Hendrix |
| 2005/0192187 A1 | 9/2005 | Wagner |
| 2005/0192188 A1 | 9/2005 | Wagner |
| 2005/0192189 A1 | 9/2005 | Wagner |
| 2005/0221334 A1 | 10/2005 | Benson |
| 2005/0238680 A1 | 10/2005 | Stella |
| 2005/0249758 A1 | 11/2005 | Di |
| 2005/0269372 A1 | 12/2005 | Smith |
| 2005/0276768 A1 | 12/2005 | Wei |
| 2005/0287088 A1 | 12/2005 | Guiramand |
| 2006/0002880 A1 | 1/2006 | Peffly |
| 2006/0008438 A1 | 1/2006 | Velarde |
| 2006/0039986 A1* | 2/2006 | Okamoto ............... A61K 8/735 424/489 |
| 2006/0040834 A1 | 2/2006 | Hilliard |
| 2006/0042184 A1 | 3/2006 | Perkins |
| 2006/0079417 A1 | 4/2006 | Wagner |
| 2006/0079419 A1 | 4/2006 | Wagner |
| 2006/0079420 A1 | 4/2006 | Wagner |
| 2006/0079421 A1 | 4/2006 | Wagner |
| 2006/0094628 A1 | 5/2006 | Wei |
| 2006/0094635 A1 | 5/2006 | Pereira |
| 2006/0182699 A1 | 8/2006 | Taylor |
| 2006/0189495 A1 | 8/2006 | Librizzi |
| 2006/0193800 A1 | 8/2006 | Reinhardt et al. |
| 2006/0210505 A1 | 9/2006 | Clapp |
| 2006/0257348 A1 | 11/2006 | Walters |
| 2006/0269501 A1 | 11/2006 | Johnson |
| 2006/0276357 A1 | 12/2006 | Smith |
| 2006/0276768 A1 | 12/2006 | Miller |
| 2007/0141001 A1 | 6/2007 | Clapp |
| 2007/0155637 A1 | 7/2007 | Smith, III |
| 2007/0187274 A1 | 8/2007 | Dalea |
| 2007/0196344 A1 | 8/2007 | Osborne |
| 2007/0202488 A1 | 8/2007 | Hendrix |
| 2007/0202489 A1 | 8/2007 | Hendrix |
| 2007/0202490 A1 | 8/2007 | Hendrix |
| 2007/0202491 A1 | 8/2007 | Hendrix |
| 2007/0224154 A1 | 9/2007 | Brumbaugh |
| 2007/0224696 A1 | 9/2007 | Honkonen |
| 2007/0248562 A1 | 10/2007 | Berry |
| 2007/0259796 A1 | 11/2007 | Fevola et al. |
| 2007/0280976 A1 | 12/2007 | Taylor |
| 2007/0286832 A1 | 12/2007 | Clapp |
| 2008/0039353 A1 | 2/2008 | Focht |
| 2008/0045428 A1 | 2/2008 | Focht |
| 2008/0045429 A1 | 2/2008 | Focht |
| 2008/0095733 A1 | 4/2008 | Griffin |
| 2008/0112913 A1 | 5/2008 | Librizzi |
| 2008/0196787 A1 | 8/2008 | Comstock |
| 2008/0233061 A1 | 9/2008 | Gates |
| 2008/0242573 A1 | 10/2008 | Wei |
| 2009/0005449 A1 | 1/2009 | Gunn |

(56) References Cited

U.S. PATENT DOCUMENTS

| | | |
|---|---|---|
| 2009/0005460 A1 | 1/2009 | Gunn |
| 2009/0028809 A1 | 1/2009 | Cetti |
| 2009/0042765 A1 | 2/2009 | Gizaw |
| 2009/0107062 A1 | 4/2009 | Pedersen |
| 2009/0148392 A1 | 6/2009 | SenGupta |
| 2009/0162443 A1 | 6/2009 | Anthony |
| 2009/0209600 A1 | 8/2009 | Miner |
| 2009/0220443 A1 | 9/2009 | Braksmayer |
| 2009/0227751 A1 | 9/2009 | Yoshinaka |
| 2009/0311348 A1 | 12/2009 | Einarsson |
| 2009/0324521 A1 | 12/2009 | Cetti |
| 2010/0022454 A1 | 1/2010 | Norskov-lauritsen |
| 2010/0022455 A1 | 1/2010 | Chilkoti |
| 2010/0022456 A1 | 1/2010 | Christensen |
| 2010/0022458 A1 | 1/2010 | Kopke |
| 2010/0028376 A1 | 2/2010 | Einarsson |
| 2010/0040074 A1 | 2/2010 | Dropps |
| 2010/0040075 A1 | 2/2010 | Kalhoff |
| 2010/0048706 A1 | 2/2010 | Subramanyam |
| 2010/0105102 A1 | 4/2010 | Hanes |
| 2010/0158830 A1 | 6/2010 | Wei |
| 2010/0184847 A1 | 7/2010 | Shin |
| 2010/0190675 A1 | 7/2010 | Cetti |
| 2010/0209374 A1 | 8/2010 | Wei |
| 2010/0216707 A1 | 8/2010 | Bernard |
| 2010/0317677 A1 | 12/2010 | Hassel |
| 2010/0322878 A1 | 12/2010 | Stella |
| 2011/0033842 A1 | 2/2011 | Moon |
| 2011/0038830 A1 | 2/2011 | Bernard |
| 2011/0045037 A1 | 2/2011 | Tamarkin |
| 2011/0045039 A1 | 2/2011 | Sunkel |
| 2011/0064688 A1 | 3/2011 | Jordan |
| 2011/0071123 A1 | 3/2011 | Schwartz |
| 2011/0089196 A1 | 4/2011 | Cetti |
| 2011/0091439 A1 | 4/2011 | Bernard |
| 2011/0117225 A1 | 5/2011 | Wei |
| 2011/0162668 A1 | 7/2011 | Coffindaffer |
| 2011/0165607 A1 | 7/2011 | Takeda |
| 2011/0245124 A1 | 10/2011 | Tsaur et al. |
| 2011/0245125 A1 | 10/2011 | Tsaur |
| 2011/0247954 A1 | 10/2011 | Wei |
| 2011/0250141 A1 | 10/2011 | Wei |
| 2011/0251872 A1 | 10/2011 | Wei |
| 2011/0253157 A1 | 10/2011 | Wei |
| 2011/0253158 A1 | 10/2011 | Wei |
| 2011/0257020 A1 | 10/2011 | Stella |
| 2011/0257030 A1 | 10/2011 | Stella |
| 2011/0257071 A1 | 10/2011 | Miralles |
| 2011/0262025 A1 | 10/2011 | Jarrold |
| 2011/0262570 A1 | 10/2011 | Finlay |
| 2011/0268802 A1 | 11/2011 | Dihora et al. |
| 2011/0269657 A1 | 11/2011 | Dihora |
| 2011/0280822 A1 | 11/2011 | Griffin |
| 2011/0281256 A1 | 11/2011 | Davis |
| 2011/0281366 A1 | 11/2011 | Davis |
| 2011/0305653 A1 | 12/2011 | Jordan |
| 2012/0009285 A1 | 1/2012 | Wei |
| 2012/0010303 A1 | 1/2012 | Mujkic |
| 2012/0035557 A1 | 2/2012 | Coffindaffer |
| 2012/0087882 A1 | 4/2012 | Fevola |
| 2012/0093753 A1 | 4/2012 | Fevola |
| 2012/0128964 A1 | 5/2012 | Hulse et al. |
| 2012/0184448 A1 | 7/2012 | Stella |
| 2012/0197016 A1 | 8/2012 | Laughlin, II |
| 2012/0258074 A1 | 10/2012 | Mills |
| 2012/0258126 A1 | 10/2012 | Schoeller |
| 2012/0276175 A1 | 11/2012 | Dihora et al. |
| 2012/0276177 A1 | 11/2012 | Hilliard, Jr. |
| 2012/0276210 A1 | 11/2012 | Dihora |
| 2012/0282309 A1 | 11/2012 | Dihora |
| 2012/0283112 A1 | 11/2012 | Binder |
| 2012/0316095 A1 | 12/2012 | Wei |
| 2013/0115610 A1 | 5/2013 | Lanzalaco |
| 2013/0115648 A1 | 5/2013 | Lanzalaco |
| 2013/0149273 A1 | 6/2013 | Wei |
| 2013/0183360 A1 | 7/2013 | Lips et al. |
| 2013/0202667 A1* | 8/2013 | An ............... A61Q 19/00 424/401 |
| 2013/0225468 A1 | 8/2013 | Corominas |
| 2013/0253057 A1 | 9/2013 | Wei |
| 2013/0280174 A1 | 10/2013 | Lipic |
| 2013/0280192 A1 | 10/2013 | Carter et al. |
| 2013/0280193 A1 | 10/2013 | Carter |
| 2013/0280202 A1 | 10/2013 | Stella |
| 2013/0280356 A1 | 10/2013 | Stella |
| 2013/0281551 A1 | 10/2013 | Stella et al. |
| 2013/0344012 A1 | 12/2013 | Cohen |
| 2014/0023606 A1 | 1/2014 | Scheunemann |
| 2014/0057997 A1 | 2/2014 | Chevalier |
| 2014/0072533 A1 | 3/2014 | Lanzalaco |
| 2014/0131395 A1 | 5/2014 | Chang |
| 2014/0197309 A1 | 7/2014 | Davis |
| 2014/0219946 A1 | 8/2014 | Hloucha |
| 2014/0273055 A1 | 9/2014 | Kerr et al. |
| 2014/0335532 A1* | 11/2014 | Finlay ............... G01N 33/5023 435/6.12 |
| 2014/0357714 A1 | 12/2014 | Braksmayer |
| 2015/0071977 A1 | 3/2015 | Dihora |
| 2015/0096582 A1 | 4/2015 | Stella |
| 2015/0098920 A1 | 4/2015 | Stella |
| 2016/0122806 A1 | 5/2016 | Amini |
| 2016/0128913 A1 | 5/2016 | Wei |
| 2016/0128927 A1 | 5/2016 | Wei |
| 2016/0128930 A1 | 5/2016 | Stella |
| 2016/0129917 A1 | 5/2016 | Gariepy |
| 2016/0215326 A1 | 7/2016 | Martin et al. |
| 2016/0310375 A1 | 10/2016 | Torres Rivera |
| 2017/0000711 A1 | 1/2017 | Jansen |
| 2017/0049673 A1 | 2/2017 | Wei |
| 2017/0165155 A1 | 6/2017 | Glenn, Jr. |
| 2017/0165164 A1 | 6/2017 | Zhao |
| 2017/0174413 A1 | 6/2017 | Callens et al. |
| 2017/0228514 A1 | 8/2017 | Apte |
| 2017/0333315 A1 | 11/2017 | Wei |
| 2018/0055894 A1 | 3/2018 | Kim |
| 2018/0110704 A1 | 4/2018 | Zhao |
| 2018/0185255 A1 | 7/2018 | Wei |
| 2018/0353394 A1 | 12/2018 | Skubsch |
| 2018/0360706 A1 | 12/2018 | Dihora |
| 2019/0117546 A1 | 4/2019 | Wei |
| 2019/0142714 A1 | 5/2019 | Dihora |
| 2019/0242880 A1* | 8/2019 | Bredif ............... G01N 33/6881 |
| 2020/0040373 A1 | 2/2020 | Wei |
| 2020/0146967 A1 | 5/2020 | Wei |
| 2020/0360251 A1 | 11/2020 | Wei |
| 2021/0077372 A1 | 3/2021 | Wei et al. |

FOREIGN PATENT DOCUMENTS

| | | |
|---|---|---|
| EP | 0078138 A2 | 5/1983 |
| EP | 1005849 B1 | 9/2001 |
| EP | 1243321 A1 | 9/2002 |
| EP | 0907345 B1 | 5/2003 |
| EP | 1657159 B1 | 8/2007 |
| EP | 2505180 A1 | 10/2012 |
| FR | 2233036 A1 | 1/1975 |
| FR | 2792728 A1 | 10/2000 |
| FR | 2924613 B1 | 6/2009 |
| GB | 2245585 A1 | 8/1992 |
| JP | S61155311 A | 7/1986 |
| JP | H0395110 A | 4/1991 |
| JP | H04149112 A | 5/1992 |
| JP | 2010235567 A | 10/2010 |
| JP | 2016183134 A | 10/2016 |
| KR | 1020110068049 A | 6/2011 |
| KR | 1020120009774 A | 2/2012 |
| KR | 20170102857 A | 9/2017 |
| WO | 9212911 A1 | 8/1992 |
| WO | 9410973 A1 | 5/1994 |
| WO | 9526710 A1 | 10/1995 |
| WO | 9534280 A1 | 12/1995 |
| WO | 9629979 A1 | 10/1996 |
| WO | 9717938 A1 | 5/1997 |
| WO | 9827193 A1 | 6/1998 |

(56) References Cited

FOREIGN PATENT DOCUMENTS

| WO | 9927904 | A1 | 6/1999 |
|---|---|---|---|
| WO | 9938491 | A1 | 8/1999 |
| WO | 9946319 | A1 | 9/1999 |
| WO | 9955303 | A1 | 11/1999 |
| WO | 0030597 | A1 | 6/2000 |
| WO | 0067712 | A1 | 11/2000 |
| WO | 0075240 | A1 | 12/2000 |
| WO | 0101931 | A2 | 1/2001 |
| WO | 0155497 | A1 | 8/2001 |
| WO | 02100358 | A1 | 12/2002 |
| WO | 2008074624 | A1 | 6/2008 |
| WO | 2008148672 | A1 | 12/2008 |
| WO | 2009081368 | A2 | 7/2009 |
| WO | 2011133538 | A1 | 10/2011 |
| WO | 2013037121 | A1 | 3/2013 |

OTHER PUBLICATIONS

D.J. Burgess, Practical Analysis of Complex Coacervate Systems, Journal of Colloid and Interface Science, vol. 140, No. 1, Nov. 1990, pp. 227-238.

J. Crank, The Mathematics of Diffusion, 2nd Edition, dated May 24, 1975, 4 pages.

Tahitian Escape Exfoliating Body Wash, XPOQ2752393, Database accession No. 1124626, Jun. 2009 (Jun. 2009) 3 Pages.

Michael Starch et al., "New Cosmetic Ingredients Based onMetathesized Soybean Oil", ip.com Journal, ip.com Inc., West Henrietta, NY, US, Sep. 9, 2010 (Sep. 9, 2010), XP013140234. 11 Pages.

Michael Starch: "New Cosmetic Ingredients Based on Soybean Oil", ip.com journal, ip.com Inc., West Henrietta NY, US, Jun. 15, 2007, pp. 6, 12, 14.

Milton, Section 9.2: Testing Hypotheses on a Proportion, Introduction to Probability and Statistics, Fourth Edition, Sep. 30, 2002, pp. 129-131.

Mintel Database "Extra Mild Moisturising Bar", XPOO2752390, Database accession No. 2527423, Sep. 2014 (Sep. 2014, 5 Pages.

Mintel Database "Healthy Shower Gel", Mar. 2011 (Mar. 2011), XP002752392. Database accession No. 1513292, 3 Pages.

Mintel Database, "Shampoo", XPO02752391, Database accession No. 2242340, Nov. 2013 (Nov. 2013), 2 Pages.

PCT International Search Report and Written Opinion for PCT/US2019/062605 dated Feb. 21, 2020, 12 pgs.

Product Data Sheet, N000557—Jun. 2009 (Year: 2009), 1 Page.

Rimpro India, Surfactant, 2011, 2 Pages.

Silva et al. Insights into the skin microbiome dynamics of leprosy patients during multi-drug therapy and in healthy individuals fromBrazil. Scientific Reports Jun. 8, 2018, 8:8783, pp. 1-10 (Year: 2018).

Triethanolamine Product Specification, Chemical Book, 2008, pp. 1-3.

Weber et al. Steroid-Free Over-the-Counter Eczema Skin Care Formulations Reduce Risk of Flare, Prolong Time to Flare, andu Reduce Eczema Symptoms in Pediatric Subjects With Atopic Dermatitis Journal of Drugs in Dermatology, 2015, vol. 14, Issue 5, pp. 478-485.

Zeng et al. High-Altitude Living Shapes the Skin Microbiome in Humans and Pigs. Frontiers in Microbiology 2017, vol. 8, article1929, pp. 1-10 (Year: 2017).

"Effects of xerosis and aging on epidermal proliferation and differentiation", Br. J. Dermatology, 137: pp. 219-225 (1997) M. Engelke.

C. Faller et al. "Predictive ability of reconstructed human epidermis equivalents for the assessment of skin irritation of cosmetics", Toxicology In Vitro., vol. 16, No. 5, Feb. 22, 2002, pp. 557-572.

Cheng Cheng Zhou et al. Self-Aggregation, Antibacterial Activity, and Mildness of Cyclodextrin/Cationic Trimeric Surfactant Complexes 11, ACS Applied Materials & Interfaces, XP055557529, vol. 8, No. 45, dated Nov. 7, 2016 (Nov. 7, 2016), pp. 30811-30823.

Clariant "Mild Surfactants Clariant Mild Surfactants for Personal Care Applications", Jul. 23, 2015, 39 Pages.

Draelos. "The effect of Cetaphil Gentle Skin Cleanser on the skin barrier of patients with rosacea", Cutis Apr. 2006, 77 (4Suppl), 2006, pp. 27-33.

Erhirhie et al. "Medicinal Values of *Citrullus lanatus* (Watermelon): Pharmacological Review", International Journal of Research in Pharmaceutical and Biomedical Sciences 2013, vol. 4, No. 4, pp. 1305-1312.

Ertel et al., "Leg wash protocol to assess the skin moisturization potential of personal cleansing products", International Journal of Cosmetic Science, vol. 21, No. 6 Dec. 1999, pp. 383-397.

FDA CFR 21 201.57 (Apr. 1, 2008 edition), p. 24-39.

Flores et al. "Microbiome of Affected and Unaffected Skin of Patients with Atopic Dermatitis Before and After Emollient Treatment", Journal of Drugs in Dermatology , 2014, vol. 13, issue 11, pp. 611-618.

Geert De Lathauwer, CD Proceeding 6th World Surfactant Congress CESIO, Berlin Germany, (paper# 154), Jun. 2004, 9 Pages.

Grando et al., "Adrenergic and Cholinergic Control in the Biology of Epidermis: Physiological and Clinical Significance", Journal of Investigative Dermatology vol. 126, 2006, pp. 1948-1965.

Grice and Segre "The skin microbiome". Nature Reviews Microbiology 2011, vol. 9, pp. 244-253.

Household Products Database, Brand Information, "Olay Daily Renewal Moisturizing Body Wash, Calming," [Online] URL: http://householdproducts.nlm.nih.gov/cgi-bin/household/brands?tbl=brands&id=16003084, accessed Feb. 8, 2006, 2 pages.

J. Caelles et al., "Anionic and Cationic Compounds in Mixed Systems", Cosmetics & Toiletries, vol. 106, Apr. 1991, pp. 49-54.

Jing, G. et al., "Parallel-META 3: Compreshensive taxonomical and functional analysis platform for efficient comparison of microbial communities", Scientific Reports, 7:40371, DOI: 10.1038/srep40371, 2017, 11 pages.

Joachim W. Fluhrl et al. "Comparative study of five instruments measuring stratum corneum hydration (Corneometer CM 820 and CM 825, Skicon 200, Nova DPM 9003, DermaLab). Part 11. In vivo", Skin Research and Technology, Jan. 1, 1999, pp. 171-178.

Josias H. Hamman et al. "Composition and Applications of Aloe Vera Leaf Gel", Published Aug. 8, 2008, Molecules 2008, 13, pp. 1599-1616.

Kikuchi et al., "Improvement of Mild Inflammatory Changes of the Facial Skin Induced by Winter Environment with Daily Applications of a Moisturizing Cream". A Half-Side Test of Biophysical Skin Parameters, Cytokine Expression Pattern and the Formation of Cornified Envelope, Dermatology, vol. 207, No. 3, 2003, pp. 269-275.

KOBO Brochure, "Treated Pigments", May 2000, 20 Pages.

Kong et al. "Performing Skin Microbiome Research: A Method to the Madness", Journal of Investigative Dermatology, 2016, vol. 137, pp. 561-568.

Kong, et al., "Temporal shifts in the skin microbiome associated with disease flares and treatment in children with atopic dermatitis", Genome Research, Published by Cold Spring Harbor Laboratory Press, 2012, vol. 22, pp. 850-859.

Meisel et al. "Skin Microbiome Surveys are strongly influenced by experimental design", Journal of Investigative Dermatology, 2016, vol. 136, pp. 947-956.

Niemeyer et al. "A systematic literature review of the human skin microbiome as biomarker for dermatological drug development". British Journal of Clinical Pharmacology 2018, vol. 84, pp. 2178-2193.

Raja K Sivamani et al: "An Epinephrine-Dependent Mechanism for the Control of UV-Induced Pigmentation", Journal of Investigative Dermatology, vol. 129, No. 3, Aug. 21, 2008, pp. 784-787.

Rogers et al., "Stratum corneum lipids: the effect of ageing and the seasons", Archives of Dermatological Research, 288, 1996, pp. 765-770.

Russel M. Walters et al., "Cleansing Formulations That Respect Skin Barrier Integrity", Dermatology Research and Practice, vol. 2012, XP055557527, Jan. 1, 2012, pp. 1-9.

Sam Osseiran et al. "Characterizing stratum corneum structure, barrier function, and chemical content of human skin with coherent Raman scattering imaging" Biomedical Optics Express, vol. 9. No. 12, Nov. 26, 2018, 19 pages.

(56) References Cited

OTHER PUBLICATIONS

Schallreuter et al., "The induction of the α-1-adrenoreceptor signal transduction system on human melanocytes", Experimental Dermatology 1996; vol. 5, Issue 1, pp. 20-23.

Scott Truong: "Design of a Handheld Skin Moisture Measuring Device for Application towards Eczema" Apr. 3, 2009, https://macsphere.mcmaster.ca/bitstream/11375/14416/1/fulltext.pdf, pp. 8, 9, 17 and 18.

Seite et al. "Using a specific cleanser for patients with mild atopic dermatitis: relationship between clinical efficacy and skin microbiota modification", SKIN The Journal of Cutaneous Medicine 2017, 1, 44, 10.25251/skin.1.supp.43, 3 pages.

Seite et al., "Barrier function and microbiotic dysbiosis in atopic dermatitis", Clinical, Cosmetic and Investigational Dermatology, vol. 8, 2015, pp. 479-483.

Sun et al., "A Microbiome-Based Index for Assessing Skin Health and Treatment Effects for Atopic Dermatitis in Children", mSystems, vol. 4, Issue 4, e00293-19, Jul./Aug. 2019, pp. 1-20.

Tate Owen, Roger Pynn, Jennifer S. Martinez, and Alison Butler; "Micelle-to-Vesicle Transition of an Iron-Chelating Microbial Surfactant, Marinobactin E", Nov. 12, 2005, Langmuir, 21,26, pp. 12109-12114.

Two et al. "The Cutaneous Microbiome and Aspects of Skin Antimicrobial Defense System Resist Acute Treatment with Topical Skin Cleansers", Journal of Investigative Dermatology 2016, vol. 136, pp. 1950-1954.

Van Oss, C.J., "Coacervation, Complex Coacervation and Flocculation", Journal of Dispersion Science, vol. 9, 1989, 14 pages.

Vaughan, C. D., "Solubility, Effects in Product, Package, Penetration and Preservation", Cosmetics and Toiletries, vol. 103, Oct. 1988, 23 Pages.

Voegeli et al., "Efficient and simple quantification of stratum corneum proteins on tape strippings by infrared densitometry", Skin Research and Technology 2007, 13, pp. 242-251.

www.single-cell.cn/skin search results retrieved Oct. 5, 2019, 1 Page.

Xu et al., "Skin benfits of moisturising body wash formulas for children with atopic dermatitis: A randomised controlled clinical study in China" Australasian Journal of Dermatology, 2019, 6 Pages.

Yogiraj et al. "Carica papaya Linn: An overview", International Journal of Herbal Medicine 2014, vol. 2, No. 5, pp. 01-08.

"Dove All Day Moisturizing Body Wash" Online URL: http://www.ewg.org/reports/skindeep2/report.php?type=PRODUCT&id=8801874, XP002332778, 6 Pages.

"The validity and practicality of sun-reactive skin types I through VI". Arch. Dermatology, 1988, 124, pp. 869-871.

\* cited by examiner

METHODS FOR SCREENING PERSONAL CARE PRODUCTS

FIELD OF THE INVENTION

The present disclosure generally relates to methods for screening personal care products utilizing skin explants.

BACKGROUND OF THE INVENTION

Over time, cleansing of the skin has become part of a personal hygiene regimen. As this regimen has been more widely adopted, companies and individuals have developed products for cleansing the skin. The skin, however, is a complex organ. At times, products that have been developed to cleanse the skin have been harmful to the skin by overly drying the skin or damaging the skin's barrier properties. While some testing methods have been developed to help screen products and understand their impact to the skin, these methods often rely on in vitro methods which are not truly predictive and/or not consumer relevant. In addition, current in vivo clinical studies are expensive, time consuming, and have a limited throughput. As such, additional screening methods for personal care products are needed.

SUMMARY OF THE INVENTION

As one example, a method of screening a rinse-off personal care composition, comprises: a. selecting a first skin explant from a first culture media; b. applying a control product to the first skin explant; c. adding water and washing the first skin explant with a control product; d. rinsing the control product from the first skin explant with water and drying the first skin explant; e. placing the first skin explant in the first culture media for about 24 hours; f. selecting a second skin explant from a second culture media; g. applying a rinse-off personal care composition to the second skin explant; h. adding water and washing the second skin explant with the rinse-off personal care composition; i. rinsing the rinse-off personal care composition from the second skin explant and drying the second skin explant; j. placing the second skin explant in the second culture media for about 24 hours; k. repeat (b) to (e) for the control product for at least two days; l. repeat (g) to (j) for the rinse-off personal care composition for at least two days; m. compare the condition of the first skin explant and the condition of the second skin explant to assess the efficacy of the control product versus the rinse-off personal care composition.

This and other examples will be more fully described below.

DETAILED DESCRIPTION OF THE INVENTION

Definitions

"Personal care composition" refers to compositions intended for topical application to skin or hair. The personal care compositions can be extrudable or dispensable from a package. Personal care compositions can be in the form of, for example, a liquid, semi-liquid cream, lotion, or gel. Examples of personal care compositions can include but are not limited to shampoo, conditioning shampoo, body wash, moisturizing body wash, shower gels, skin cleansers, cleansing milks, hair and body wash, in shower body moisturizer, pet shampoo, shaving preparations, and cleansing compositions used in conjunction with a disposable cleansing cloth.

"Rinse-off" as used herein refers to a composition which is applied topically to the skin and/or hair and is intended to be subsequently rinsed from the skin and/or hair with water within seconds to a few minutes of application. An example of a product which is rinse-off is a body wash. The product could also be wiped off using a substrate.

Personal care products, like personal cleansers, can help to maintain the skin. Cleansers can help to remove dirt, debris, and other materials from the skin. Cleansers can also impact the skin's moisture, barrier, and other properties. Before a company decides to put a new cleanser on the market, they may want to test the product to understand its impact to the skin or to understand its performance for particular attributes or in certain circumstances.

Testing of this sort can be done in a variety of ways. For example, a cleanser can be placed in a tube and shaken in order to approximate the foam the product will generate during use. When it comes to measuring the impact of a product on the skin, this can be more complicated. Companies can run a clinical study utilizing volunteer subjects, but these tests can be very expensive, can take a long time, and are often limited in the number of products that can be tested at one time. Likewise, tests conducted on skin mimics or artificial skin can give results that are difficult to relate back to real skin or are just not good at predicting the impact on real skin as they can lack the interconnectivity, permeability, and or complexity of human skin.

A beneficial way to test personal care products is with explant skin. Explant skin is skin that has been removed from a person during a medical procedure, like a panniculectomy. The use of actual skin has its advantages. It is less costly than a clinical study, where there is testing on live human subjects, and allows for the screening of more products (i.e. higher throughput). In addition, the results allow for a more in depth understanding of the mechanistic nature of the product's impact on skin.

One downside to the use of explant skin is that it has limited viability. In order to prolong the viability of the skin explant, the explant can be cultured. For example, the explant can be placed into a container with an appropriate culture medium. One example of a suitable culture medium is Dulbecco's Modified Eagle Medium. The culture medium provides nutrients to the skin explant. The culture medium may be iso-osmotic or non-osmotic. The culture medium can include additional additives like an anti-mycotic agent, an antibacterial agent, an amino acid, a vitamin, or a combination thereof. In addition, the subcutaneous layer of the skin explant can be removed to improve absorption of the media into the explant during culturing. An example of explant skin preparation is included in Example 1 below.

As part of the culturing process, a porous membrane may be used. Such membranes are generally placed underneath the skin explant such that the membrane is in the media and the media feeds the skin explant through capillary action through the membrane. It may be desirable to select a membrane that permits the media to pass through it at a particular rate, based on the size and/or type of skin sample. One example of a suitable membrane is the Millipore® brand.

Another mechanism for optimizing the viability of a skin explant is through its storage parameters. These can include for example, time, temperature, humidity, carbon dioxide level, etc. Skin explants can be cultured for example, for about 2 days to about 19 days, about 5 days to about 19 days, about 5 days to about 14 days, about 5 days to about 10 days, or about 6 days to about 8 days. A culturing temperature can be, for example, from 33° C. to 40° C., from 35° C. to 40° C., or even from 36° C. to 38° C. may be suitable, although other temperatures may be acceptable based on the target attribute. Humidity levels for culturing of a skin explant can be, for example, less than 100% humidity, from 40% to 90% humidity, from 50% to 70% humidity, or at a low humidity range of less than 30%, or 20% to 30% humidity. The carbon dioxide level may be, for example, 5%.

In addition, storage parameters can be manipulated to simulate skin conditions. For example, storage conditions can be set to a low humidity, like 20-30%, to simulate winter conditions and/or to generate skin explants which mimic dry skin.

Explant skin can be used to screen for efficacy of personal care compositions. This testing can be done to assess a personal care composition versus a control, like water, or to compare compositions one to the other. Efficacy of a personal care composition could be directed to moisture content of the skin explant. Personal care compositions can impact the moisture content of skin. Change in moisture content of a skin explant can imply the product could have a drying impact on skin (for a decrease in moisture content versus water), a neutral impact (meaning there was relatively no change versus water), or could be moisturizing (for an increase in moisture content versus water). Likewise, where a personal care composition is compared to a second composition, the moisture content of a skin explant can imply differences or similarities in the products with respect to their drying, neutrality, or moisturizing impacts.

Moisture content of a skin explant can be measured in accordance with industry standard testing. Some examples of methods for measuring moisture content of a skin explant include epidermal conductance, epidermal capacitance, bio-impedance, diffusion, and combinations thereof. Epidermal conductance can be measured with a moisture pen. The probe of a moisture pen can be placed on a skin explant where it can measure the level of moisture in the skin and/or give a notification if a skin explant exceeds a preset level of moisture. One example of a moisture pen is manufactured by DermaLab.

Epidermal capacitance can be measured with a corneometer. A corneometer can be used to measure the moisture of a skin explant by placing a probe against the skin explant. The corneometer uses capacitance measurement of a dielectric medium to detect hydration level. One example of a corneometer is Corneometer® CM 825 manufactured by Courage-Khazaka Electronic.

Bioimpedance can be measured utilizing a Skicon instrument. A Skicon instrument can be used to measure the moisture of a skin explant by placing the probe on the skin explant. One example of an acceptable Skicon instrument is the Skicon-200® manufactured by the IBS Company.

Efficacy of a personal care composition can also be assessed by looking at moisture diffusion from a skin explant. Personal care compositions can impact the ability of the skin barrier to retain moisture. The level of moisture loss through the skin explant can imply whether a personal care composition will impact the skin barrier. Level of diffusion of moisture of a skin explant can be measured as transepidermal water loss. If the level of transepidermal water loss is higher than that of a water control or a comparison product then the test product may have a negative impact on skin barrier function, if it is the same or similar, then it has a neutral impact (versus a water control or is similar in efficacy to a comparison product), or if water loss is less than that of a water control or comparison product then then the product may have no impact or less of an impact on barrier function than the control or test products. Transepidermal water loss can be measured with an instrument, like an AquaFlux™ by Nokorode® or with a VapoMeter manufactured by the Delfin Company. Transepidermal water loss is measured by placing a skin explant in a cylinder with two sensors that measure the partial pressure of the water vapor from the skin explant and the gradient between the two sensors is directly proportional to the rate of evaporation.

Efficacy of a personal care composition could also be detected by cell metabolic activity in the skin explant. Personal care compositions can impact the metabolic activity of the cells in the skin explant. The level of metabolic activity in the cells of a skin explant can imply whether a personal care composition will impact the condition of the skin explant. If the level of cell metabolic activity of a test product is higher than that of a water control or a comparison product then the test product is more efficacious (i.e. better for the skin), if it is the same or similar, then it has a neutral impact (versus a water control or is similar in efficacy to a comparison product), or if cell metabolic activity is less than that of a water control or comparison product then the test product is less efficacious (i.e. worse for the skin).

Cell metabolic activity can be assessed by an MTT assay. An MTT assay uses NAD(P)H-dependent cellular oxidoreductase enzymes to reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. Rapidly dividing cells exhibit high rates of MTT reduction.

Efficacy of a personal care composition could also be evaluated by measuring the level of a protein related to cell proliferation. One example of such a protein in the Ki67 protein. Personal care compositions can impact the level of the Ki67 protein of the cells in the skin explant. The level of Ki67 protein in the cells of a skin explant can imply whether a personal care composition will impact the underlying health of the skin explant. If the level of Ki67 protein is higher than that of a water control or a comparison product then the test product is better for the underlying condition of the skin explant, if it is the same or similar, then it has a neutral impact (versus a water control or is similar in efficacy to a comparison product), or if Ki67 protein level is less than that of a water control or comparison product then the test product is worse for the underlying condition. The level of Ki67 protein can be measured by a Ki67 staining assay.

Efficacy of a personal care composition can be evaluated by measuring the level of expression of the Natural Moisturization Factor (NMF) biomarkers. NMF biomarkers correlate to a skin explant's ability to maintain its hydration level. Personal care compositions can impact the level of expression NMF biomarkers in the skin explant. The level of NMF biomarker expression in a skin explant can imply whether a personal care composition will impact the ability of the skin to maintain hydration. If the level of NMF biomarker expression is higher than that of a water control or a comparison product then the test product is better at retaining the ability of the skin explant to maintain hydration, if it is the same or similar, then it has a neutral impact (versus a water control or is similar in efficacy to a comparison product), or if the level of expression of NMF biomarkers is less than that of a water control or comparison product then the test product is worse at retaining the ability of the skin to maintain hydration. The level of expression of NMF biomarkers can be measured by standard analytical instruments such as a mass spectrometer.

Efficacy of a personal care composition can also be evaluated by measuring the level of apoptotic DNA fragmentation. One example of a way to measure this is a TUNEL assay. A TUNEL assay can utilize terminal Deoxynucleotidyl transferase tagged with a marker to determine the level of apoptosis. Personal care compositions can impact the level of apoptotic DNA fragmentation in the skin explant. The level of apoptotic DNA fragmentation of a skin explant can imply whether a personal care composition will impact the underlying health of the skin explant. If the level apoptotic DNA fragmentation is higher than that of a water control or a comparison product then the test product is worse for the underlying condition of the skin explant, if it is the same or similar, then it has a neutral impact (versus a water control or is similar in efficacy to a comparison product), or if the level of apoptotic DNA fragmentation is less than that of a water control or comparison product then the test product is better for the underlying condition.

As noted above, explant skin was used to evaluate a rinse-off personal care composition for efficacy. Explant skin was procured and prepared for use. Preparation for use can include, for example, washing and drying, removal of the subcutaneous layer, cutting of the explant skin into appropriately sized pieces, etc. The skin explant was placed in a culture medium. On day 1, prior to product application, a baseline measurement was taken of moisture, MTT skin viability, Ki67 positive cells, and TUNEL positive cells. After the baseline measurement, test product is applied to the skin. In this instance the test products (water, a first personal care composition (Test A), and a second personal care composition (Test B)), are applied to separate pieces of explant skin.

Figure 1:
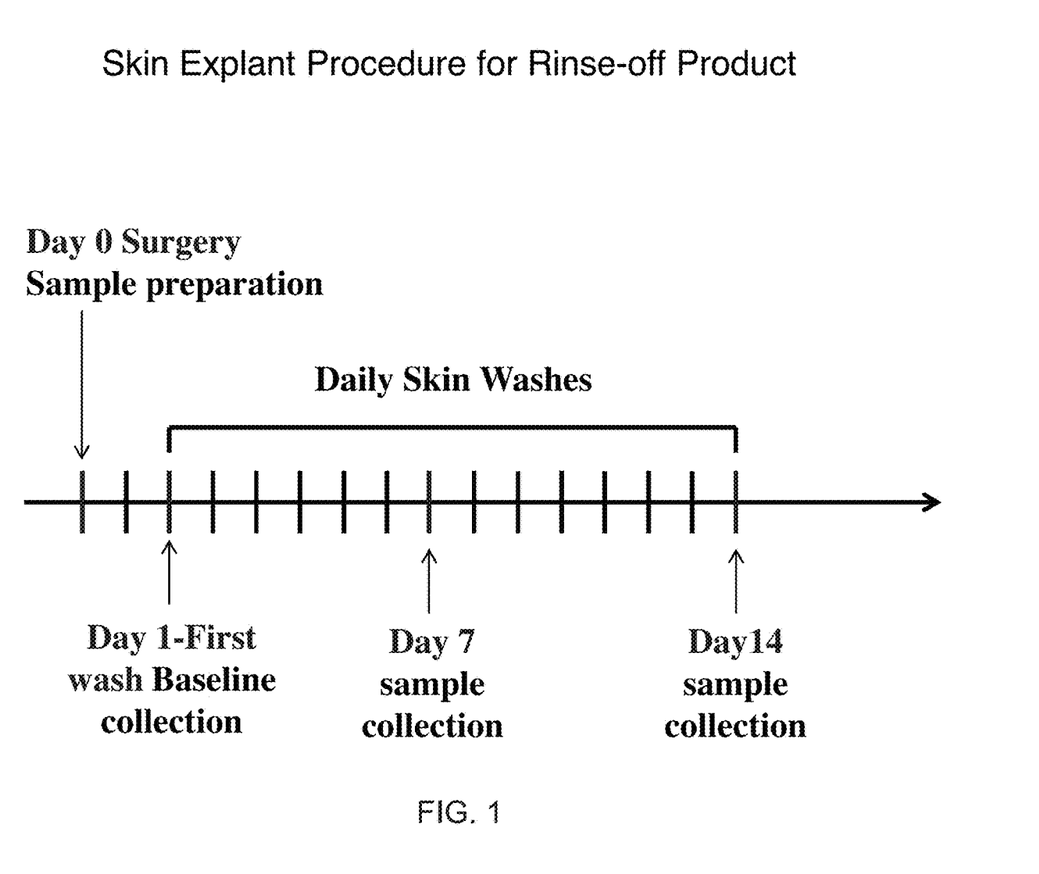
FIG. 1 is a graph showing an exemplary timeline for evaluation of a personal care composition with a skin explant.
Figure 2:
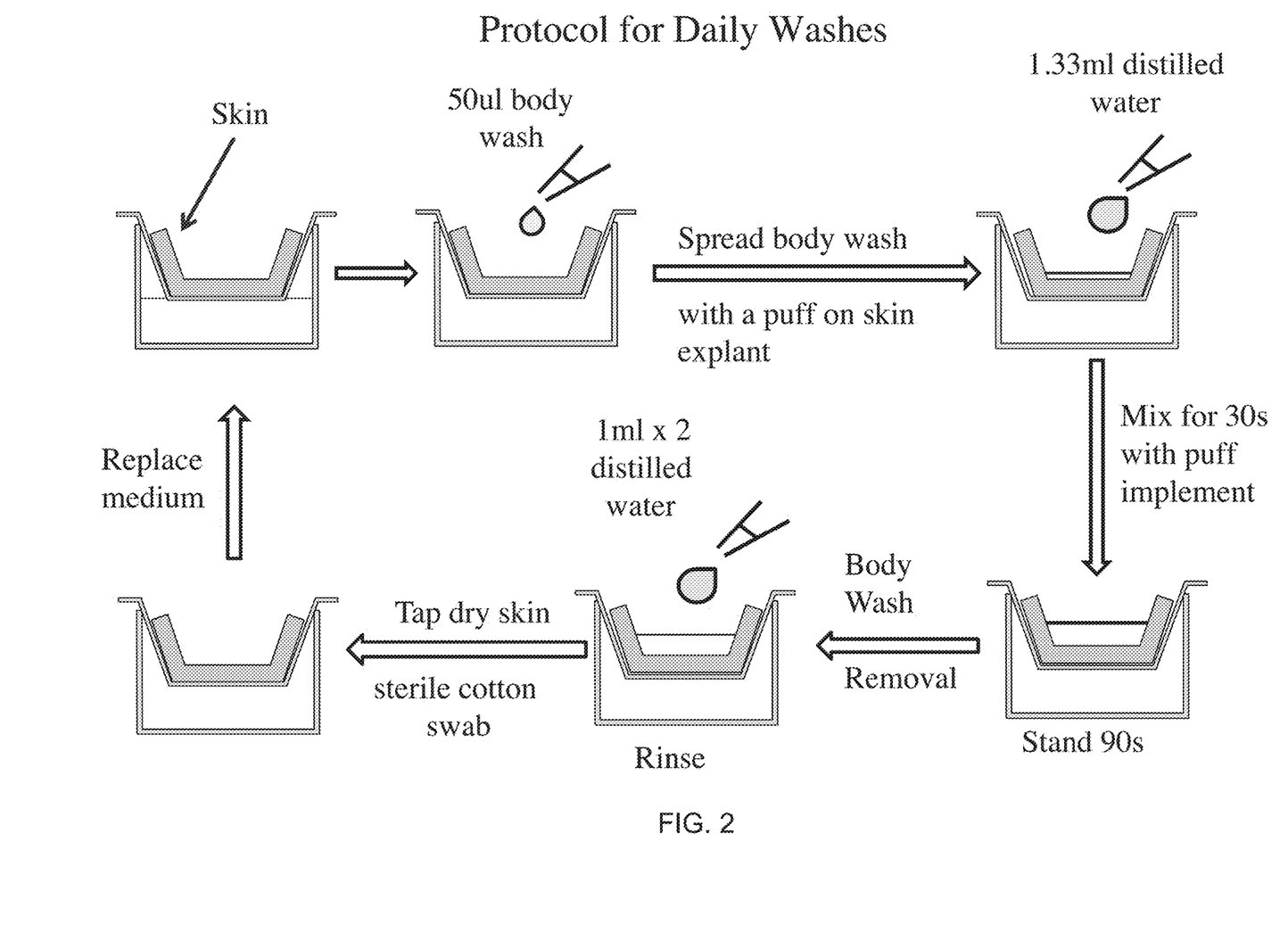
FIG. 2 is a graphic representation of an exemplary daily washing procedure as noted in FIG. 1.

The personal care compositions can be applied as shown in FIG. 2. The explant skin is removed from the media culture and placed in a beaker. 50 µL of a personal care composition is applied to a piece of explant skin in the beaker. The personal care composition is spread on the explant skin using a puff. 1.33 mL of distilled water is then added to the beaker. The puff is then used to wash the epidermis side of the explant skin for 30 seconds. The explant skin is left in the beaker for 90 seconds. The liquid in the beaker with the explant skin is then removed by pouring off the liquid. The explant skin is then rinsed twice, each time with 1 mL of distilled water. The explant skin is removed from the rinse water and tapped dry with sterile cotton. The explant skin is then placed in a container with fresh culture medium. Where the test product is water, it is applied as if it were a personal care composition described above. The test products can be applied once a day for 14 days, as exemplified in FIG. 1, with testing occurring on days 1, 7, and 14.

Figure 3:
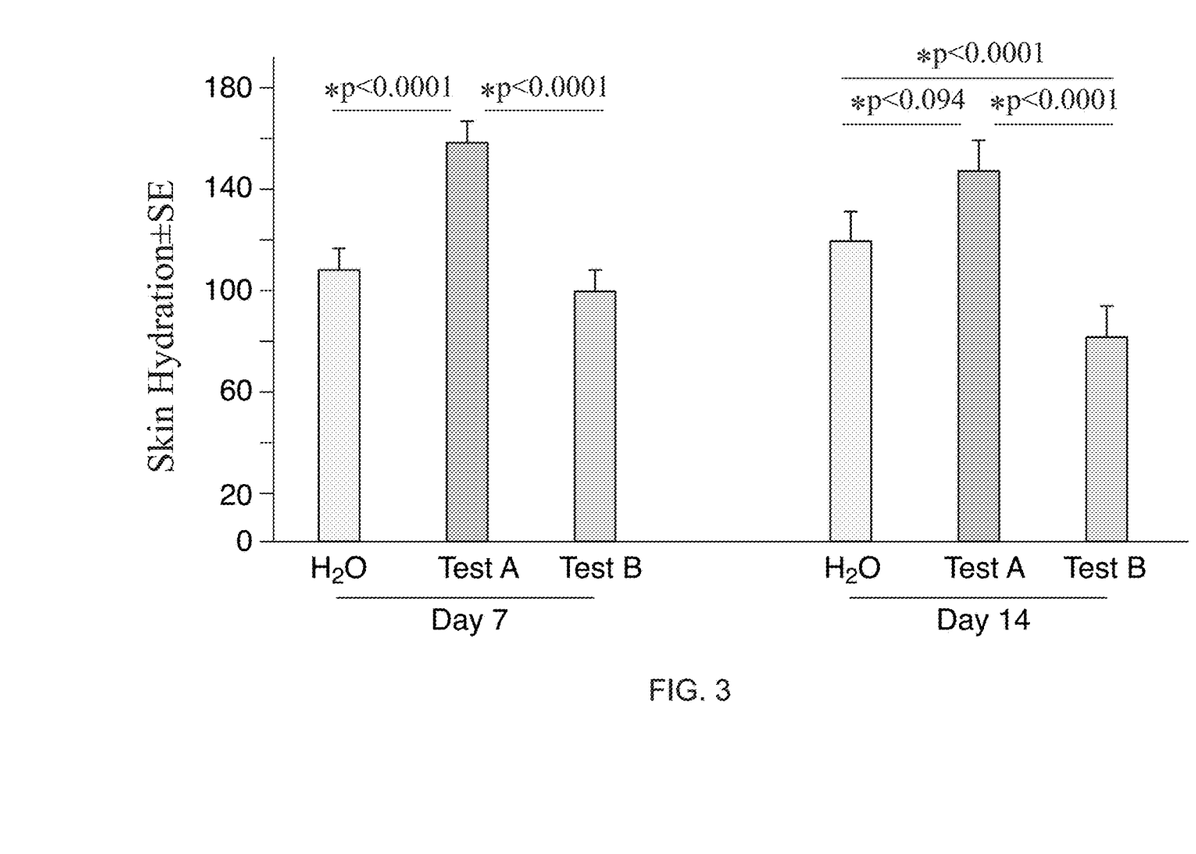
FIG. 3 is a graph showing skin hydration of skin explant treated with water, Personal Care Product (Test A), Personal Care Product (Test B) at days 7 and 14 as measured by a moisture pen.

The moisture of the skin explant for the water control, personal care composition Test A (A) and personal care composition Test B (B) is measured at baseline, day 7, and day 14 as noted in FIGS. 1 and 3. The moisture is measured with a moisture pen. The moisture pen is placed on the surface of the skin explant, where it gives a moisture reading. As can be seen from FIG. 3, personal care compositions Test A and Test B, as well as the water control are measured with a moisture pen. The skin explant on which Personal care composition A was placed had a significantly higher moisture level than both the water control and personal care composition B at both 7 and 14 days. This shows Test A had better skin moisturization than the water control and Test B.

Figure 4:
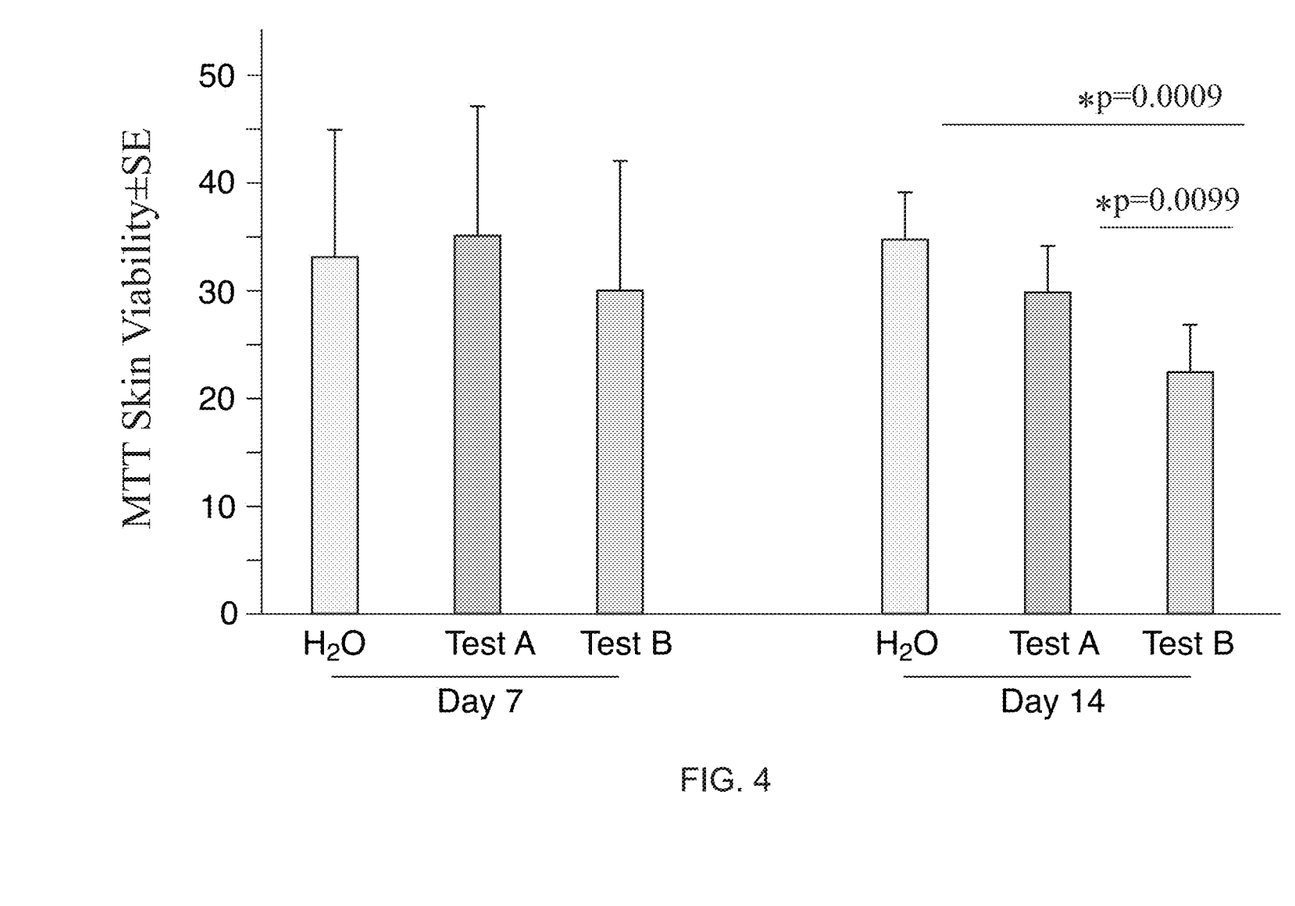
FIG. 4 is a graph showing MTT skin viability of skin explant treated with water, Personal Care Product (Test A), Personal Care Product (Test B) at days 7 and 14 as measured by an MTT assay.

As can be seen in FIG. 4, the skin explants with water control, personal care composition Test A, and personal care composition Test B are tested for MTT skin viability. At day 7, MTT skin viability was higher for personal care composition Test A than both the water control and personal care composition Test B and is higher than personal care composition B at the 14-day time period. This shows Test composition A had better cell viability and skin condition than the water control and composition Test B.

Figure 5:
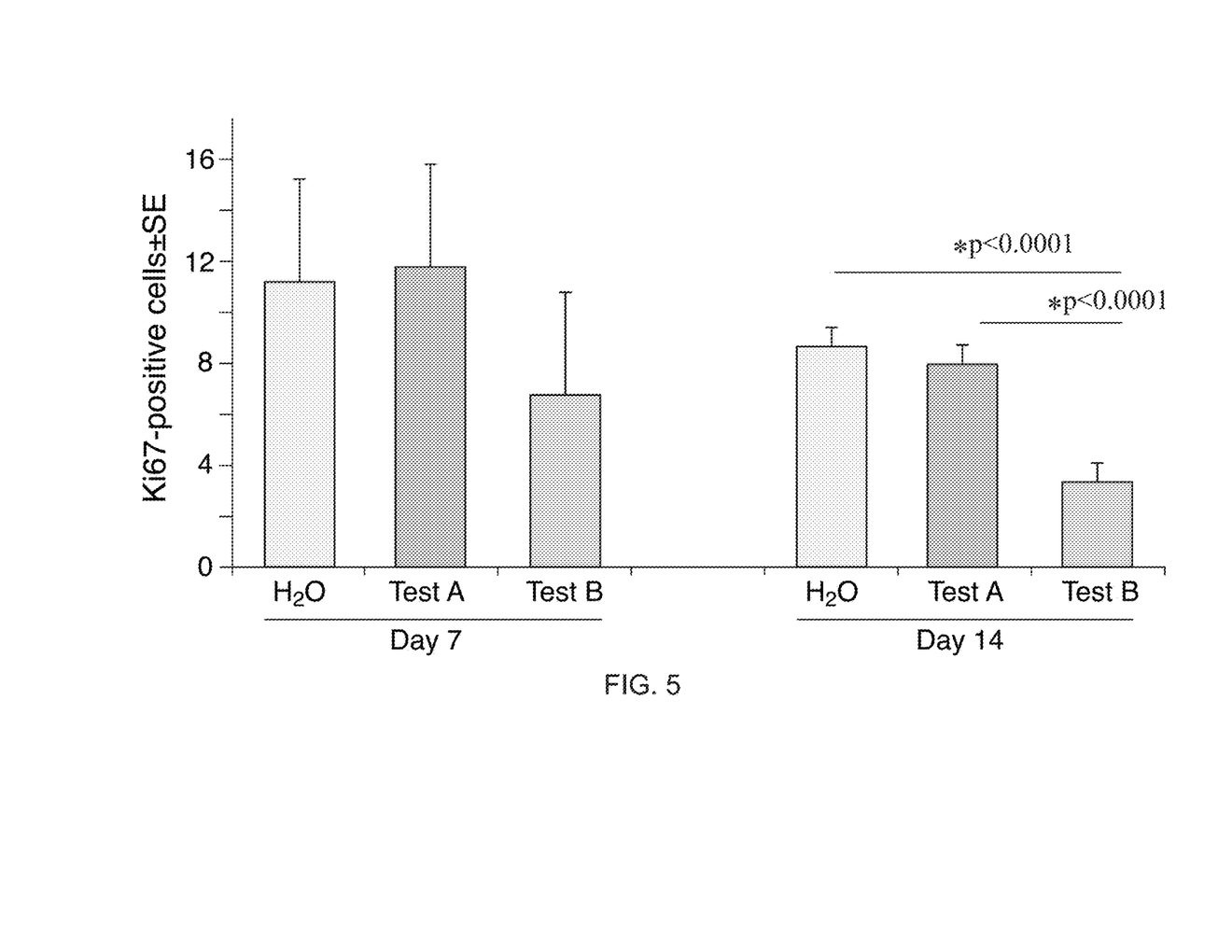
FIG. 5 is a graph showing Ki67 activity levels in skin explant treated with water, Personal Care Product (Test A), Personal Care Product (Test B) at days 7 and 14 as measured by a Ki67 staining method.

Explant skin contacted with personal care composition Test A, personal care composition Test B, and a water control are also tested at days 7 and 14 for Ki67 viability. At day 7, Ki67 viability was higher for personal care composition A than both the water control and personal care composition B and is higher than personal care composition B at the 14-day time period (see FIG. 5). This shows composition Test A had better Ki67 viability and skin condition than the water control and composition test B.

Figure 6:
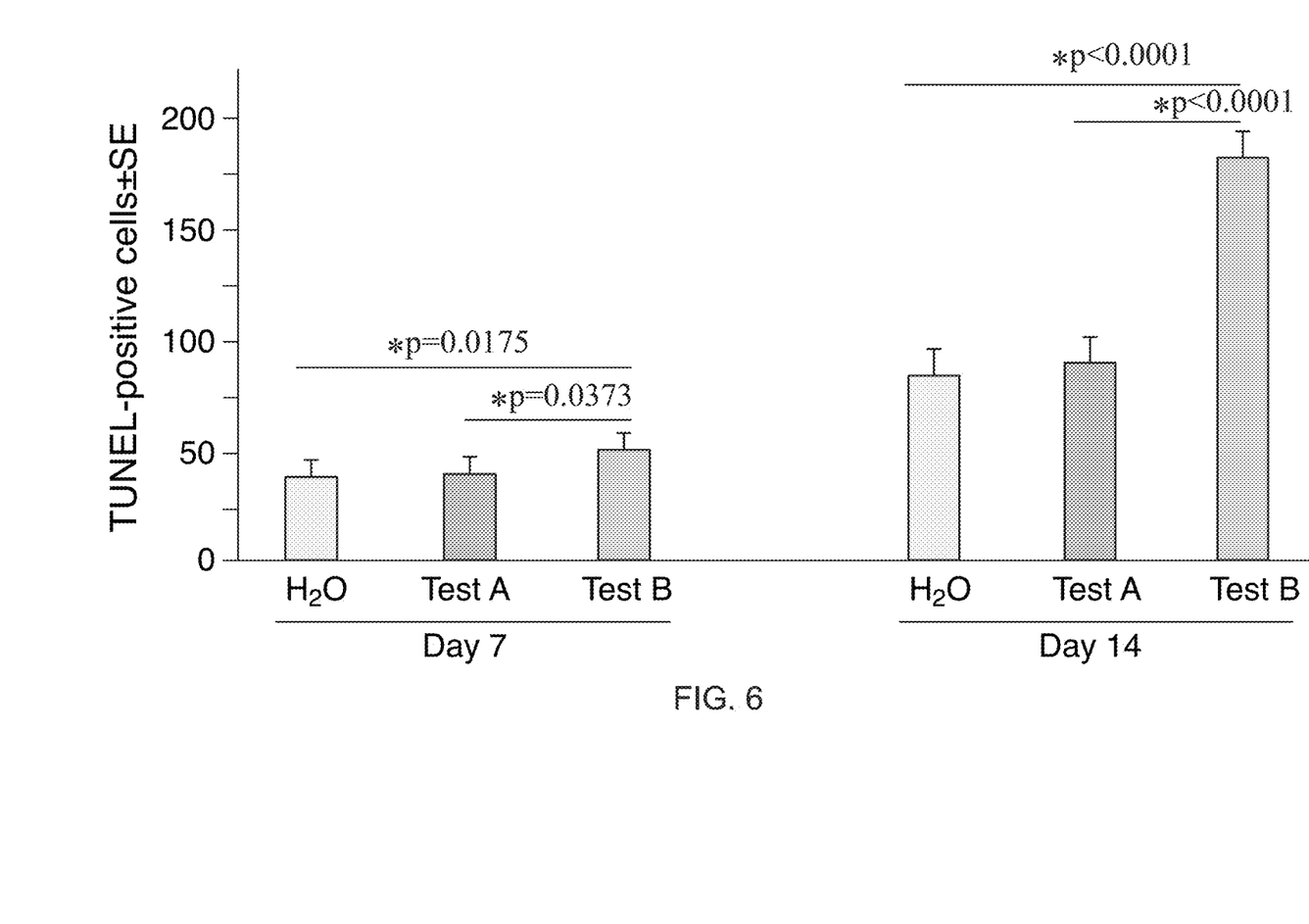
FIG. 6 is a graph showing TUNEL positive cells in a skin explant treated with water, Personal Care Product (Test A), Personal Care Product (Test B) at days 7 and 14 as measured by a TUNEL assay.

FIG. 6 shows results of testing of personal care composition Test A, personal care composition Test B, and a water control are also tested at days 7 and 14 for expression of TUNEL in the cells. Personal care composition Test A is similar to that of the water control and less than that of personal care composition Test B at day 7 and is far less than personal care composition Test B at day 15. This shows product A may have similar cell toxicity vs. water control while product B performed worse in cell toxicity vs. water control and product A.

Taken together, Test product A had significantly better performance in skin hydration and impact on underlying skin condition versus the water control and Test product B.

EXAMPLES

Example 1—Skin Explant Preparation

Materials for preparation include: Dulbecco's Modified Eagle Medium plus Glutamax, antibiotic and antimycotics, 1× phosphate buffer solution (PBS (−ca, −mg), 150 mm×15 mm sterile culture dishes, sterile gauze 4×4, disposable safety scalpels, 4 mm disposable biopsy punch, 6-well cell culture inserts, disinfected tweezers, cotton-tipped applicators, 6-well culture plates, ruled, disinfected cutting mat, optionally with a 12×12 ruler, scraper handle, tissue freezing medium, biopsy cassettes, frozen tissue freezing vessels, 10% formalin, shipping containers for fixed tissue, and biohazard/sharps containers.

Skin preparation can involve preparation of media in advance of the arrival of skin (3× media including 500 ml DMEM plus 15 ml of antibiotic and antimycotics; the 3× referred to 3-fold levels of antibiotics/antimycotics used for the initial hour of incubation; 1× Media: 500 ml DMEM plus 5 ml of antibiotic and antimycotics).

On arrival, the skin is removed from the package and soaked in 3×DMEM media and stored at 4° C. for 1 hour. After 1 hour, the skin is removed from the 3×DMEM and rinsed with sterile 1×PBS. The skin is placed in a clean culture dish containing gauze soaked with 1×DMEM. The sample can be put in culture the same day as arrival; though the sample may be stored overnight at 4° C. if desired.

In preparation for culture, the following can be performed on the skin tissue. On a cutting mat, the skin tissue is positioned such that the epidermis is down, and the fat is exposed. The fat is removed with a disposable scalpel by carefully grasping one corner of the skin with sterile serrated forceps and scraping the fat away with the blade held at a 45-degree angle to the skin. After the fat is removed, the surgical edges can be cut off with a scalpel using a scraper as a straight edge guide and to hold the skin in place. Using the scraper as a guide, the skin can be cut into the desired shape and size, such as 1.25 cm wide strips using a ruler (such as the one optionally provided on the cutting mat) to measure the width. The strip is rinsed in a 100 mm culture dish containing 1×PBS. The strips are cut into 1.25 cm squares and placed in a 100 mm culture dish onto 1×DMEM soaked gauze until they are put into culture 30 minutes later (with time points of 15 minutes, 30 minutes, 45 minutes, or an hour being used in various non-limiting examples).

Example 2

Personal care composition Test A is a commercial body wash called Olay™ Ultra Moisture Body Wash. The key ingredients are: water, petrolatum, sodium trideceth sulfate, sodium chloride, cocamidopropyl betaine, trideceth-3, fragrance, *Butyrospermum parkii* (shea butter), guar hydroxypropyltrimonium chloride, sodium benzoate, xanthan gum, glyceryl oleate, disodium EDTA, citric acid, sodium hydroxide, acrylates/C10-30 alkyl acrylates cross polymer, etc. This product can be made utilizing standard industry protocol.

Example 3

Personal Care composition Test B is a commercial body wash called Dove™ Deep Moisture. The key ingredients are: water, cocamidopropyl betaine, sodium hydroxypropyl starch phosphate, lauric acid, sodium lauroyl glycinate, sodium lauroyl isethionate, hydrogenated soybean oil, *Glycine soja* (soybean) oil or *Helianthus annus* (sunflower) seed oil, sodium chloride, glycerin, fragrance, guar hydropyltrimonium chloride, DMDM Hydantion, stearic acid, citric acid, BHT, tetrasodium EDTA, etc. This product can be made utilizing standard industry protocol.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of screening a rinse-off personal care composition for a dry-skin benefit, comprising:
   a) selecting a first skin explant from a first culture media, wherein the first skin explant is cultured at a humidity level of 20% to 30% to mimic dry skin;
   b) applying a control product to the first skin explant;
   c) adding water and washing the first skin explant with the control product;
   d) rinsing the control product from the first skin explant with water and drying the first skin explant;
   e) placing the first skin explant in the first culture media for about 24 hours;
   f) selecting a second skin explant from a second culture media, wherein the second skin explant is cultured at a humidity level of 20% to 30% to mimic dry skin;
   g) applying the rinse-off personal care composition to the second skin explant;
   h) adding water and washing the second skin explant with the rinse-off personal care composition;
   i) rinsing the rinse-off personal care composition from the second skin explant and drying the second skin explant;
   j) placing the second skin explant in the second culture media for about 24 hours;
   k) repeat (b) to (e) for the control product for at least two days;
   l) repeat (g) to (j) for the rinse-off personal care composition for at least two days;
   m) compare the condition of the first skin explant and the condition of the second skin explant to assess the efficacy of the control product versus the rinse-off personal care composition.

2. The method of claim 1, wherein the efficacy of the control product versus the rinse-off personal care composition is assessed by moisture content, wherein more moisture content is more efficacious.

3. The method of claim 2, wherein the moisture content is measured via epidermal conductance, epidermal capacitance, bioimpedance, diffusion, or a combination thereof.

4. The method of claim 3, wherein the conductance is measured with a moisture pen.

5. The method of claim 3, wherein the epidermal capacitance is measured by a corneometer.

6. The method of claim 1, wherein the efficacy of the control product versus the rinse-off personal care composition is assessed by cell metabolic activity, wherein more cell metabolic activity is more efficacious.

7. The method of claim 6, wherein cell metabolic activity is assessed by an MTT assay.

8. The method of claim 1, wherein the control product is water.

9. The method of claim 1, wherein the control product is a second personal care composition.

10. The method of claim 1, wherein (k) and (l) are repeated once a day for 3 days to 28 days.

11. The method of claim 1, wherein (k) and (l) are repeated once a day for 5 days to 21 days; once a day for 5 days to 14 days, or once a day for 7 days to 10 days.

* * * * *